US006303296B1

(12) United States Patent
Bensimon et al.

(10) Patent No.: US 6,303,296 B1
(45) Date of Patent: *Oct. 16, 2001

(54) PROCESS FOR ALIGNING MACROMOLECULES BY PASSAGE OF A MENISCUS AND APPLICATIONS

(75) Inventors: David Bensimon, Paris; Aaron Bensimon, Antony; François Heslot, Viroflay, all of (FR)

(73) Assignee: Institut Pasteur Centre National de la Recherche Scientifique, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 08/687,617

(22) PCT Filed: Feb. 10, 1995

(86) PCT No.: PCT/FR95/00165

§ 371 Date: Oct. 16, 1996

§ 102(e) Date: Oct. 16, 1996

(87) PCT Pub. No.: WO95/21939

PCT Pub. Date: Aug. 17, 1995

(30) Foreign Application Priority Data

Feb. 11, 1994 (FR) .................................................. 94 01574
Jun. 17, 1994 (FR) .................................................. 94 07444

(51) Int. Cl.⁷ ............................. C12Q 1/68; C12P 19/34; G01N 33/53; C07H 21/04

(52) U.S. Cl. .................................. 435/6; 435/5; 435/91.1; 435/91.2; 435/7.1; 435/7.2; 435/7.9; 536/23.1; 536/24.3; 536/24.32; 536/24.33; 530/300; 530/350; 530/388.1

(58) Field of Search .................................. 435/6, 5, 91.2, 435/91.1, 7.1–7.2, 7.9; 536/24.3, 24.33, 24.32, 23.1; 530/300, 350, 388.1

(56) References Cited

U.S. PATENT DOCUMENTS

| 5,624,711 | 4/1997 | Sundberg et al. . |
| 5,840,862 | * 11/1998 | Bensimon et al. .................. 536/22.1 |

FOREIGN PATENT DOCUMENTS

| 37 17 210 | 12/1988 | (DE) . |
| 0 127 438 | 12/1984 | (EP) . |
| 0 391 674 | 10/1990 | (EP) . |
| 0 578 148 | 1/1994 | (EP) . |
| WO93/22463 | 11/1993 | (WO) . |
| WO97/06278 | 2/1997 | (WO) . |

OTHER PUBLICATIONS

Schwartz et al., Science, vol. 262, No. 5130, Oct. 1, 1993, pp. 110–114.

Parra et al., Nature Genetics, vol. 5, Sep. 1993, pp. 17–21.

Zimmerman et al., Nucleic Acids Research, vol. 22, No. 3, Feb. 11, 1994, pp. 492–497.

* cited by examiner

*Primary Examiner*—Jeffrey Fredman
(74) *Attorney, Agent, or Firm*—Finnegan, Henderson, Farabow, Garrett & Dunner, L.L.P.

(57) ABSTRACT

A process for aligning a macromolecule on the surface S of a support comprises forming a triple line S/A/B (meniscus) resulting from contact between a solvent A and the surface S and a medium B is caused to move on the surface S. The macromolecule has a part, especially an end, anchored on the surface S. The other part, especially the other end, is in solution in the solvent A. A process for detecting, measuring the intramolecular distance of, separating and/or assaying a macromolecule in a sample using the process of alignment is provided.

85 Claims, 10 Drawing Sheets

PROCESS FOR ALIGNING MACROMOLECULES BY PASSAGE OF A MENISCUS AND APPLICATIONS

BACKGROUND OF THE INVENTION

The present invention relates to a method for aligning macromolecules such as polymers or macromolecules with biological activity, especially DNA, or proteins. The present invention also relates to the application of this method in processes for detecting, for measuring intramolecular distance, for separating and/or for assaying a macromolecule in a sample.

Controlling the conformation of macromolecules represents a major industrial challenge, for example in the manufacture of sensors or of controlled molecular assemblies, or alternatively in problems of detection and analysis. It may be useful to have an elongated molecular conformation. By way of example, in the case where polymers are grafted on a substrate, it has been proposed to extend them by the action of an electric field, a flow or with the aid of optical tweezers. In particular, in biology, the alignment of DNA—by electrophoresis (Zimmermann and Cox Nucl. Acid Res. 22, p 492, 1994), free flow (Parra and Windle, Nature Genetics, 5, p 17, 1993 and WO 93/22463) or in a gel (Schwartz et al. Science 262, p 110, 1993 and U.S. Pat. No. 33,531) or with the aid of optical tweezers (Perkins et al., Science 264 p 819, 1994 and also U.S. Pat. No. 5,079,169)—opens numerous possibilities in mapping, or in the detection of pathogens.

These methods only allow in general an imperfect alignment, or alternatively a transient alignment—that is to say that relaxation of the molecule occurs once the stress disappears. In the case of optical tweezers, the method is expensive, is limited to only one molecule at a time, and is difficult to carry out by non-qualified staff.

A special technique for aligning DNA by flow after cell lysis, followed by drying, has been proposed (I. Parra and B. Windle and WO 93/22463). The alignment obtained is very imperfect and nonhomogeneous and numerous nonaligned masses are observed.

SUMMARY OF THE INVENTION

The subject of the present invention is a novel and simple method for aligning macromolecules on the surface S of a support, characterized in that the triple line S/A/B (meniscus) resulting from the contact between a solvent A and the surface S and a medium B is caused to move on the said surface S, the said macromolecules having a part, especially an end, anchored on the surface S, the other part, especially the other end, being in solution in the solvent A.

It has been observed according to the present invention that the mere passage of a meniscus over molecules of which one part is anchored on a substrate, the remainder of the molecule existing freely in solution makes it possible to align them uniformly, perpendicularly to the moving meniscus, leaving them adsorbed on the surface behind the meniscus. This phenomenon is called "molecular combing" here.

BRIEF DESCRIPTION OF THE DRAWINGS

The following description is made with reference to the accompanying Figures in which.

DEDTAILED DESCRIPTION OF THE INVENTION

Figure 1:
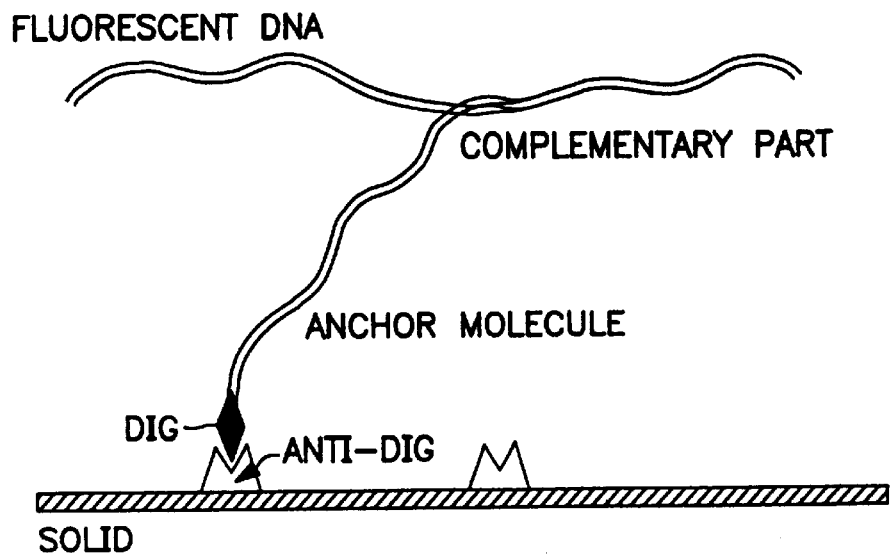
FIG. 1 schematically represents the detection of a pathogen in a fluorescent DNA molecule by hybridization with an anchor molecule.
Figure 2:
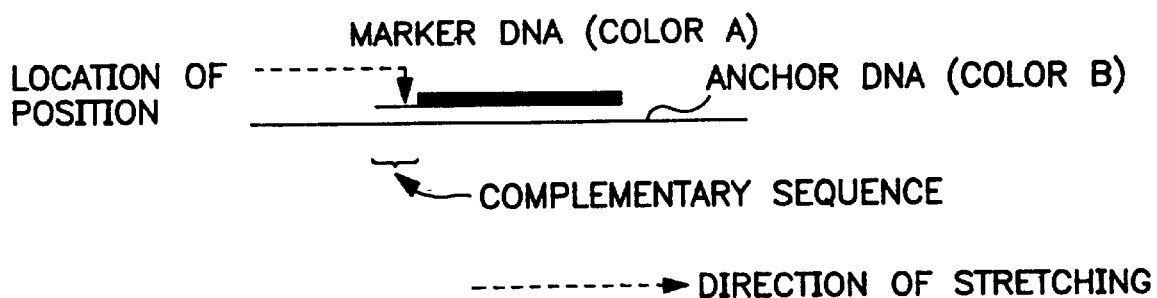
FIG. 2 schematically represents genetic mapping by extension of DNA and the use of a marker DNA.
Figure 3:
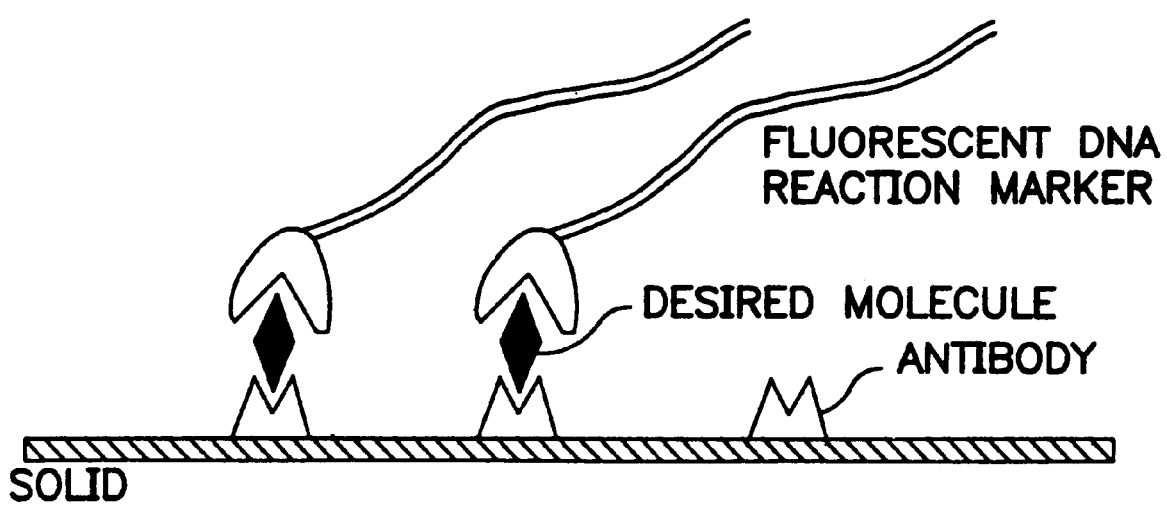
FIG. 3 schematically represents the detection of an immunological reaction (ELISA) by means of a "flag" molecule: a fluorescent DNA used as reaction marker.
Figure 4:
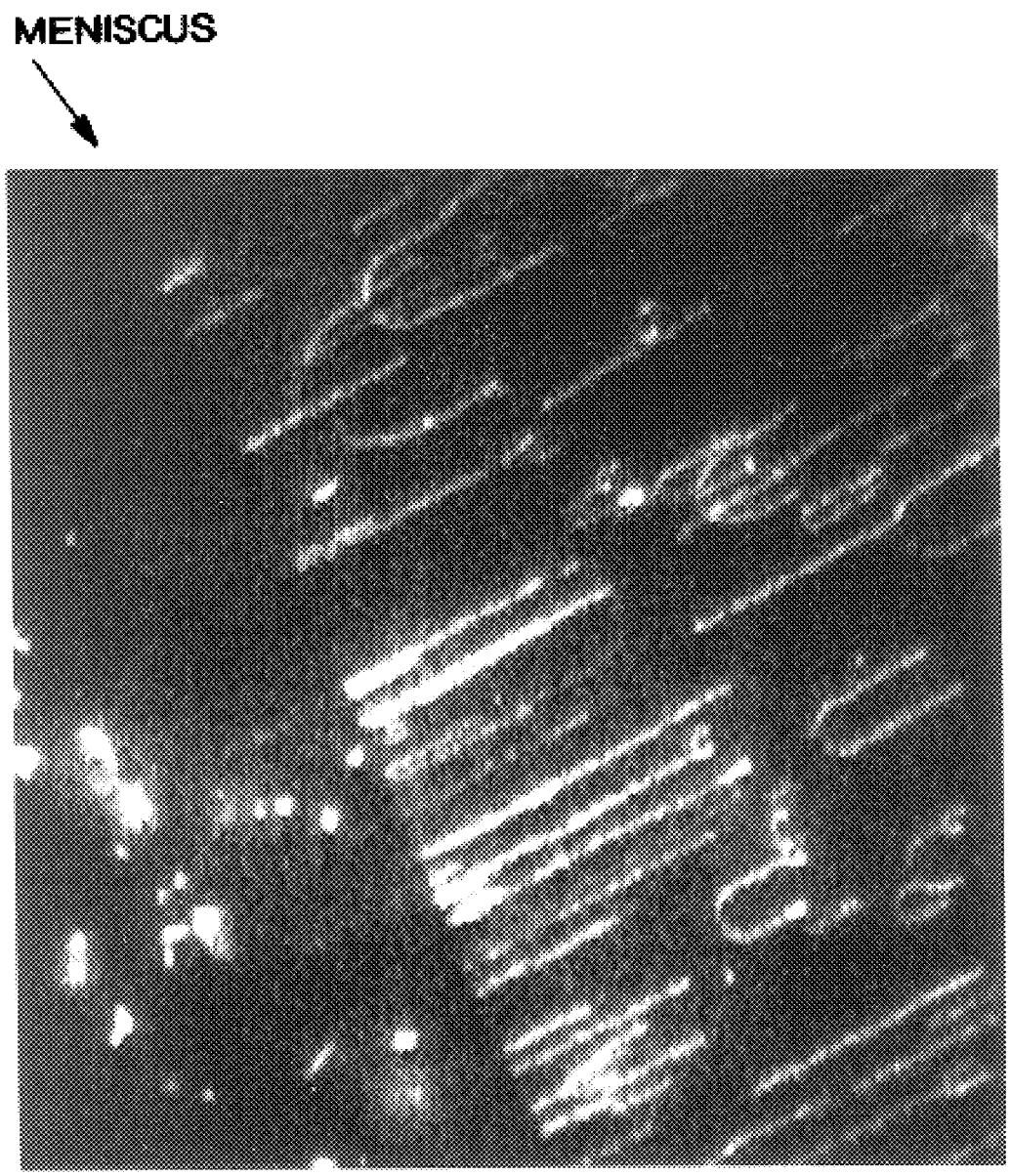
FIG. 4 is a fluorescence micrograph showing the extension of λ phage DNA by the progression of a meniscus, DNA molecules in solution stretched by the evaporation flow parallel to the meniscus can be seen on the left, DNA molecules in the open air after being stretched perpendicularly to the meniscus can be seen on the right.
Figure 5A:
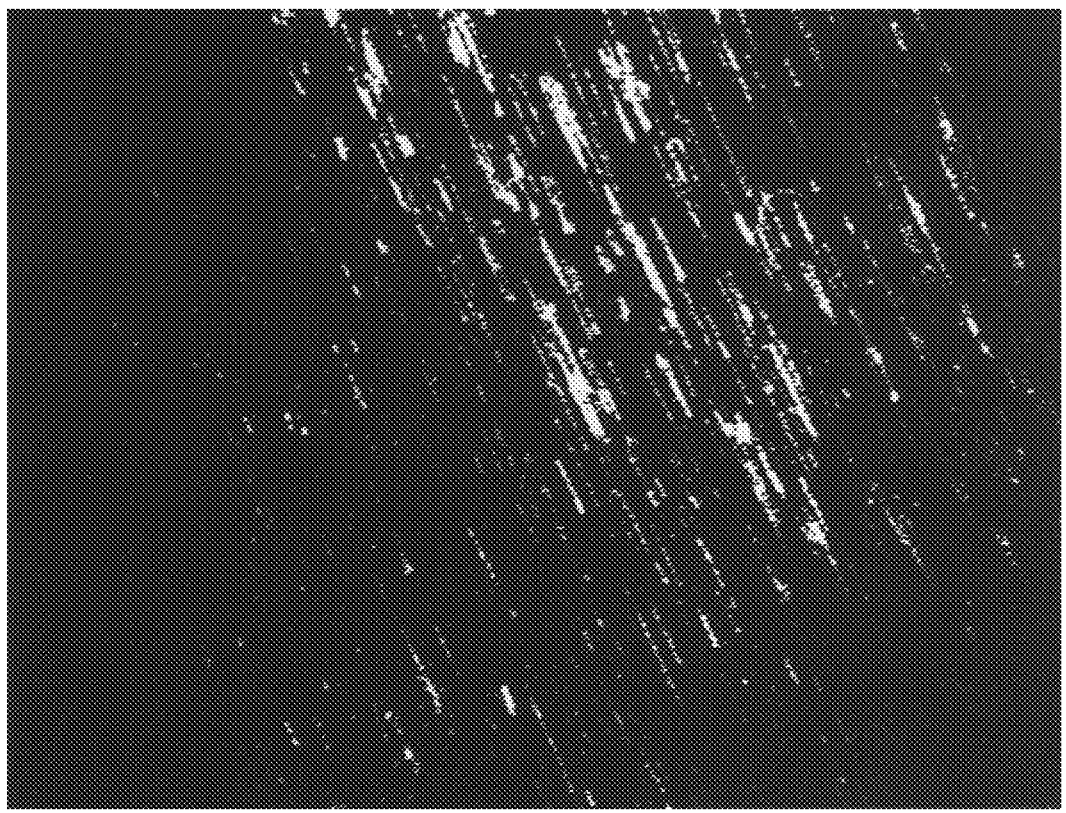
FIGS. 5(a) and 5(b) are fluorescence micrographs showing, respectively, a DNA labeled with digoxixenine (DIG) on a surface coated with anti-DIG and stretched by the meniscus, and, as control, an unlabeled DNA on an anti-DIG surface. The very high specificity of the surfaces and the absence of nonspecific anchoring will be noted.
Figure 5B:
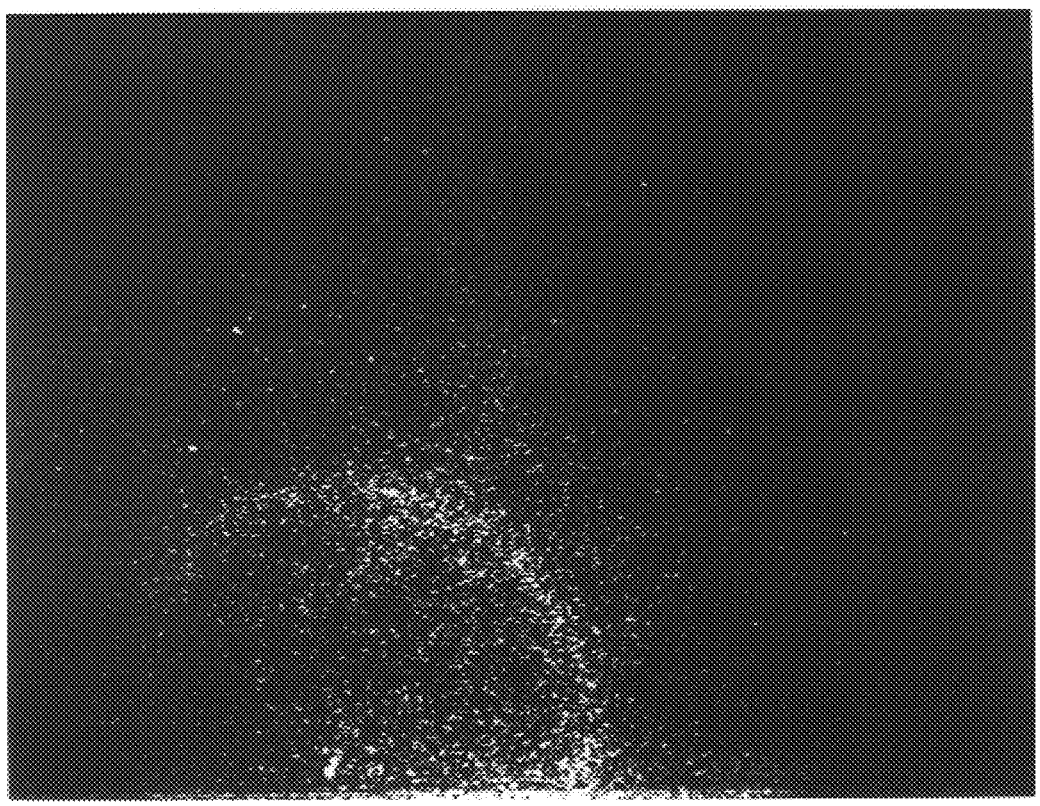
Figure 6:
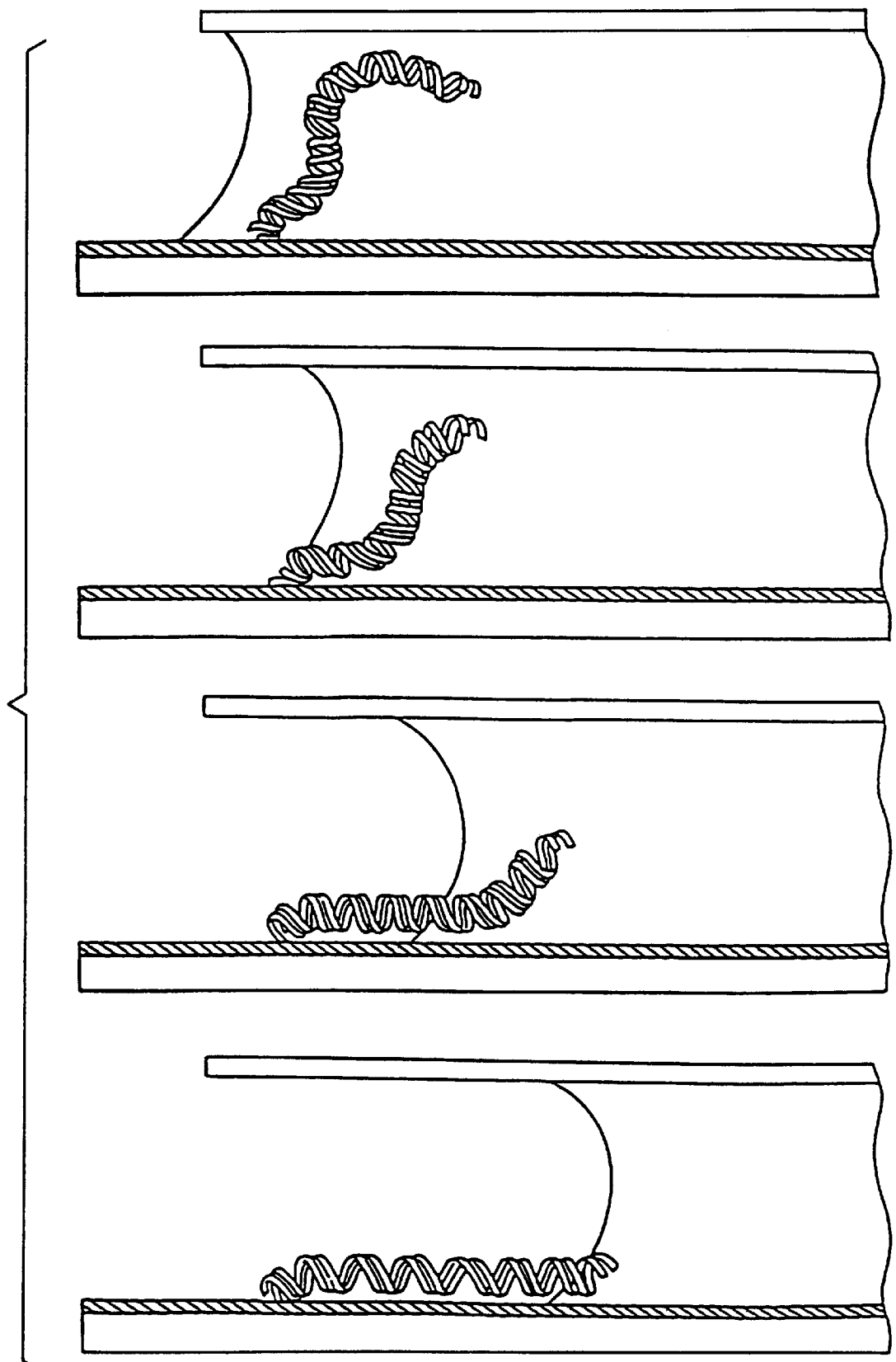
FIG. 6 is a schematic representation of the spread of DNA by passage of a meniscus. The DNA in solution is anchored on a treated surface. The DNA solution is covered with an untreated round cover slip.

More specifically, the stretching of the free part of the molecule is achieved by the passage of the triple line S/A/B constituting the meniscus between the surface S, the solvent A and a medium B which may be a gas (in general air) or another solvent.

In a specific embodiment, the meniscus is a water/air meniscus, that is to say that the solvent A is an aqueous solution and the medium B is air.

Furthermore, it is possible to extend the air/water meniscus used here in order to stretch the molecule to other systems such as oil/water or water/surfactant/air, in particular.

The movement of the meniscus can be achieved by any means of relative movement of the fluids A and B relative to the surface S. In one embodiment, the surface S can be removed from the solvent A or conversely, the solvent A can be removed from the surface S.

In particular, the meniscus can be moved by mechanical means, especially by pneumatic means by aspirating or blowing a gas, or especially by hydraulic means by pushing or aspirating the solvent A or the medium B.

Thus, the movement of the meniscus can be achieved by gradual evaporation of the solvent A.

When the movement of the meniscus is achieved mechanically, it can be achieved either by translation of the interface A/B, or by translation of the surface S.

In a specific embodiment, the solvent is placed between two supports of which at least one corresponds to the said support of surface S and the meniscus is moved for example by evaporation.

By "support", there is understood here any substrate whose cohesion is sufficient to withstand the passage of the meniscus.

The support may consist, at least at the surface, of an organic or inorganic polymer, a metal especially. gold, a metal oxide or sulfide, a semiconductor element or an oxide of a semiconductor element, such as silicon oxide or a combination thereof, such as glass or a ceramic.

There may be mentioned more particularly glass, surface-oxidized silicon, graphite, mica and molybdenum sulfide.

As "support", there may be used a single support such as a slide, beads, especially polymer beads, but also any form such as a bar, a fiber or a structured support, and also particles, whether it be powders, especially silica powders, which can moreover be made magnetic, fluorescent or colored as known in the various assay technologies.

The support is advantageously in the form of cover slips. Preferably, the support has little or no fluorescence.

Macromolecules, such as ordinary polymers, or biological polymers such as DNA, RNA or proteins, can be anchored. by ordinary methods on a support.

The macromolecule to be aligned can be chosen from biological macromolecules such as proteins, especially antibodies, antigens, ligands or their receptors, nucleic acids, DNA, RNA or PNA, lipids, polysaccharides or derivatives thereof.

It was observed according to the present invention, that the stretching force acts locally within the immediate vicinity of the meniscus. It is independent of the length of the molecule, of the number of molecules anchored, and within a wide range, of the speed of the meniscus. These characteristics are particularly important for aligning the molecules homogeneously and reproducibly.

It is possible, according to the present invention, to add surfactant elements into the solvent A and/or the medium B, which modify the properties of the interfaces. According to the present invention, the stretching can indeed be controlled by the addition of surfactants, or by an adequate surface treatment.

Too high a surface-macromolecule attraction (for example an excessively high level of adsorption) can interfere with the alignment of the molecules by the meniscus, these molecules remaining adsorbed at the surface in a state which is not necessarily stretched. Preferably, the surface exhibits a low rate of adsorption of the said macromolecule, such that only the anchored molecules will be aligned, the others being carried by the meniscus.

However, it is possible to vary the differences in adsorption between a part of the macromolecule, especially its ends, and its other parts (in particular for long molecules such as DNA or collagen) in order to anchor, by adsorption, the molecules by a part, especially their end(s) alone, the remainder of the molecule existing freely in solution, on a wide variety of surfaces and align them by the passage of the meniscus as described above.

The adsorption of a macromolecule onto a surface can be easily controlled by means of the pH or of the ionic medium content of the medium or of an electric voltage applied over the surface. The surface charges and the electrostatic (repulsive or attractive) interactions between the surface and the molecule are thus changed, thereby making it possible to pass from a state of complete adsorption of the molecule onto the surface to a total absence of adsorption. Between these two extreme cases, there is a range of control parameters where the adsorption occurs preferably through the end of the molecules and which will therefore be used advantageously to anchor them on the surface, and then to align them by the passage of the meniscus.

Once aligned, the molecules adhere strongly to the surface. In the case of DNA, it was possible to observe them by fluorescence several months after their alignment.

The present invention is therefore very different from the method proposed by Parra and Windle, because according to the present invention, the molecules are anchored on the surface and then uniformly aligned by the passage of the meniscus, whereas in the Parra and Windle method, a hydrodynamic flow is used to stretch the molecules nonhomogeneously, which molecules will become nonspecifically adsorbed onto the surface.

Other techniques can also result in the stretching and the alignment of molecules. Thus, a dynamic orientation of molecules in solution, anchored at one end, can be obtained by electrophoresis or by a hydraulic flow. However, the results observed show that these techniques are much less efficient than the use of the meniscus.

By "anchoring" of the macromolecule on the surface, there should be understood an attachment resulting from a chemical reactivity both through a covalent linkage and a noncovalent linkage such as a linkage resulting from physicochemical interactions, such as adsorption, as described above.

This anchorage of the macromolecule can be achieved directly on (or with) the surface, or indirectly, that is to say via a linkage such as another molecule, especially another molecule with biological activity. When the anchorage is achieved indirectly, the macromolecule can be grafted chemically on the said linkage, or can interact physicochemically with the said linkage, in particular when the said intermediate linkage is a molecule with biological activity recognizing and interacting with the said macromolecule.

In one embodiment, the macromolecule and the said linkage are both molecules with biological activity which interact, such as an antigen and an antibody respectively, complementary nucleic acids or lipids. In these cases, the noncovalent attachment of the macromolecule consists of a linkage of the type: antigen-antibody, ligand-receptor, hybridization between complementary nucleic acid fragments or hydrophobic or hydrophilic interaction between lipids.

Advantage is thus taken of the very high specificity and the very high selectivity of certain biological reactions, especially antigen-antibody reactions, DNA or RNA hybridization reactions, interprotein reactions or avidin/streptavidin/biotin type reactions, as well as reactions of ligands and their receptors.

Thus, in order to carry out the direct or indirect anchoring of the macromolecule on the surface S it is possible to use a solid surface having certain specificities. It is in particular possible to use certain pretreated surfaces which make it possible to attach certain proteins or DNA, whether modified or otherwise.

Such surfaces are commercially available (Covalink, Costar, Estapor, Bangs, Dynal for example) in various forms having at their surface COOH, $NH_2$ or OH groups for example.

It is, in this case, possible to functionalize the DNA with a reactive group, for example an amine, and carry out a reaction with these surfaces. However, these methods require specific functionalization of the DNA to be attached.

A technique allowing anchorage without prior treatment of the DNA has also been described. This process consists in causing a free phosphate at the 5' end of the DNA molecule to react with a secondary amine of the surface (NH Covalink surface).

Anchoring by adsorption can be achieved by adsorption of the end of the molecule by controlling the surface charge by means of the pH, the ionic content of the medium or the application of an electric voltage over the surface given the differences in adsorption between the ends of the molecule and its middle part. According to the present invention, nonfunctionalized DNA molecules were thus anchored, by way of example, on surfaces coated with molecules ending with a vinyl or amine group such as polylysine molecules, or various surfaces such as glass, coated with silane type molecules ending with vinyl or amine groups or alternatively glass cover slips previously cleaned in an acid bath. In this latter case, the surface of the glass indeed has SiOH groups.

In all these cases, the pH range where the DNA is anchored is chosen to be between a state of complete adsorption and an absence of adsorption, the latter being situated at a more basic pH. It is understood that this technique is very general and can be extended by persons skilled in the art to numerous types of surfaces.

It is also possible to functionalize the DNA with a first reactive group or a protein $P_0$ in order to cause it to react with a surface coated with a second reactive group or with a protein $P_1$, which are capable of reacting specifically with each other respectively, that is to say for example $P_1$ with $P_0$. The $P_0/P_1$ pair may be a pair of the type: biotin/streptavidin (Zimmermann and Cox) or digoxigenin/antibody directed against digoxigenin (anti-DIG) for example (Smith et al., Science 258, 1122 (1992)).

Preferably, the anchoring surfaces will have a low fluorescence level so as not to interfere with the detection of the molecules after their alignment, in particular if the detection is done by fluorescence.

According to the present invention, a solid support having, under the reaction conditions, a surface having an affinity for only part of the macromolecule, the rest of the macromolecule remaining freely in solution, is preferably used.

In one embodiment, a solid support is used which has at the surface at least one layer of an organic compound having, outside the layer, an exposed group having an affinity for a type of molecule with biological activity which may be the said molecule itself or a molecule recognizing and/or interacting with it.

The support can therefore have a surface coated with a reactive group or with a molecule with biological activity.

By "affinity", there should be understood here both a chemical reactivity and an adsorption of any type, this under optional conditions of attachment of the molecules onto the exposed group, modified or otherwise.

In one embodiment, the surface is essentially compact, that is to say that it limits access by the macromolecule with biological activity to the inner layers and/or to the support, this in order to minimize nonspecific interactions.

It is also possible to use surfaces coated with a reactive exposed group (for example $NH_2$, COOH, OH, CHO) or with a macromolecule with biological activity (for example: proteins, such as streptavidin or antibodies, nucleic acids such as oligonucleotides, lipids, polysaccharides and derivatives thereof) which is capable of attaching an optionally modified part of the molecule.

Thus, surfaces coated with streptavidin or with an antibody according to known processes ("Chemistry of Protein Conjugation and Cross-linking", S. C. Wong, CRC Press (1991)) are capable of attaching a macromolecule having, at a specific site, a biotin or an antigen.

Likewise, surfaces treated so as to have single-stranded oligonucleotides can serve in order to anchor on them DNAs/RNAs having a complementary sequence.

Among the surfaces having an exposed reactive group, there may be mentioned those on which the exposed group is a —COOH, —CHO, $NH_2$, —OH group, or a vinyl group containing a double bond —CH=$CH_2$ which is used as it is or which can be activated so as to give especially —CHO, —COOH, —$NH_2$ OR OH groups.

The supports with highly specific surfaces according to the present invention can be obtained using various processes. There may be mentioned by way of example:

(A) a layer of carbon-containing, optionally branched, polymer at least 1 nm thick, having reactive groups as defined below and (B) surfaces obtained by depositing or anchoring on a solid support one or more molecular layers; the latter can be obtained by forming successive layers attached through noncovalent linkages, as non-limiting example, Langmuir-Blodgett films, or by molecular self assembly, this allowing the formation of a layer attached by covalent linkage.

In the first case, the surface can be obtained by polymerization of at least one monomer generating at the surface of the polymer the said exposed group, or alternatively by partial depolymerization of the surface of a polymer to generate the said exposed group, or alternatively by deposition of polymer.

In this process, the polymer formed has vinyl linkages such as a polyene derivative, especially surfaces of the synthetic rubber type, such as polybutadiene, polyisoprene or natural rubber.

In the second case, the highly specific surface contains:

on a support, a substantially monomolecular layer of an organic compound of elongated structure having at least:

an attachment group having an affinity for the support, and an exposed group having no or little affinity for the said support and the said attachment group under attachment conditions, but optionally having, after chemical modification following the attachment, an affinity for one type of biological molecule.

The attachment can first of all be of the noncovalent type, especially of the hydrophilic/hydrophilic and hydrophobic/hydrophobic type, as in Langmuir Blodgett films (K. B. Blodgett, J. Am. Chem. Soc. 57, 1007 (1935).

In this case, the exposed group or the attachment group will be either hydrophilic or hydrophobic, especially alkyl or haloalkyl groups such as $CH_3$, $CF_3$, $CHF_2$, $CH_2F$, the other group being hydrophilic.

The attachment can also be of the covalent type, the attachment group will, in this case, react chemically with the support.

Certain surfaces of similar structure have already been mentioned in the electronic field, especially when the attachments are covalent, L. Netzer and J. Sagiv, J. Am. Chem. Soc. 105, 674 (1983) and U.S. Pat. No. 4,539,061.

Among the attachment groups, there must be mentioned more particularly the groups of the metal alkoxide or semiconductor type, for example silane, especially chlorosilane, silanol, methoxy- and ethoxysilane, silazane, as well as phosphate, hydroxyl, hydrazide, hydrazine, amine, amide, diazonium, pyridine, sulfate, sulfonic, carboxylic, boronic, halogen, acid halide, aldehyde groups.

Most particularly, as attachment group, groups capable of cross-reacting with an adjacent equivalent group, to give cross-linkages will be preferably used; for example they will be derivatives of the metal alkoxide or semiconductor type, for example silane, especially dichlorosilane, trichlorosilane, dimethoxysilane or diethoxysilane and trimethoxy- or triethoxysilane.

The choice of the attachment group will obviously depend on the nature of the support; the silane-type groups are quite suitable for covalent attachment on glass and silica.

As regards the exposed groups, irrespective of the surface, they will be preferably chosen from ethylenic groups, acetylenic groups or aromatic radicals, primary, tertiary or secondary amines, esters, nitriles, aldehydes, halogens. But they may be most particularly the vinyl group; indeed, the latter can be either chemically modified after attachment to give, for example, a carboxylic group or derivatives of carboxylic groups such as alcohol groups, aldehyde groups, ketone groups, acidic groups, primary, secondary or tertiary amines, or to lead to a pH-dependent direct anchoring of the biological macromolecules such as nucleic acids and proteins, without chemical modification of the surface or of the macromolecules.

Preferably, the chains connecting the exposed group to the attachment group are chains carrying at least 1 carbon atom, preferably more than 6 and in general from 3 to 30 carbon atoms.

As regards the support itself, the use of glass, surface-oxidized silicon, a polymer or gold with or without pretreatment of the surface, is generally preferred.

In the case of glass or silica, there can be used advantageously the known techniques for surface functionalization using silane derivatives, for example: Si—OH Cl$_3$—Si—R—CH=CH$_2$ gives Si—O—Si—R—CH=CH$_2$, R consisting for example of (CH$_2$)$_4$. Such a reaction is known in literature, with the use of ultrapure solvents. The reaction leads to a layer of molecules having their C=C end at the surface exposed to the outside.

In the case of gold, this being optionally in the form of a thin layer on a substrate, the known techniques for surface functionalization use thiol derivatives, for example: Au+HS—R—CH=CH$_2$ gives Au—S—R—CH=CH$_2$, R consisting for example of (CH$_2$)$_4$. Such a reaction is described in liquid medium and leads, like the preceding trichlorosilane-silica reaction, to a layer of molecules having their C=C end at the surface exposed to the outside.

Of course, the term "support" encompasses both a single surface such as a slide, but also particles, either silica powder or polymer beads, and also ordinary forms such as a bar, a fiber or a structured support, which can moreover be made magnetic, fluorescent or colored, as is known in various assay technologies.

Preferably, the support will be chosen so as to have no or little fluorescence when the detection will be carried out by fluorescence.

The surfaces obtained according to methods (A) or (B) above have:
(i) a very low level of intrinsic fluorescence, when necessary, a fluorescence background noise (with a typical surface area of 100×100 µm) smaller than the fluorescence signal of a single molecule to be detected;
(ii) the possibility of detecting isolated molecules with an S/N ratio independent of the number of molecules, which is possible by virtue of various techniques with a high S/N ratio which are described below and which are based on the identification of the presence of a macroscopic marker having a weak nonspecific interaction with the surface.

The surfaces thus obtained are preferably coated with a macromolecule with biological activity chosen from:
proteins,
nucleic acids
lipids
polysaccharides and derivatives thereof.

Among the proteins, there should be mentioned antigens and antibodies, ligands, receptors, but also products of the avidin or streptavidin type, as well as derivatives of these compounds.

Among the RNAs and DNAs, there should also be mentioned the α, β derivatives as well as the thio derivatives and mixed compounds such as PNAs.

It is also possible to attach mixed compounds such as glycopeptides and lipopolysaccharides for example, or alternatively other elements such as viruses, cells in particular, or chemical compounds such as biotin.

The attachment of the biological macromolecules may be covalent or noncovalent, for example by adsorption, hydrogen bonds, hydrophobic, ionic interactions for example, in which case cross-linking can be advantageously carried out in the molecules grafted by known methods ("Chemistry of Protein Conjugation and Cross-linking", S. C. Wong, CRC Press (1991)) and this in order to enhance their cohesion.

As mentioned above, it is possible to have an exposed group which allows direct reaction with molecules with biological activity, but it is also possible to envisage that the exposed group is treated, after attachment, so as to be converted, as indicated above, to a hydroxyl, amine, alcohol, aldehyde, ketone, COOH radical or a derivative of these groups before attachment of the biological molecule.

When such groups were exposed, techniques for attachment of proteins and/or of DNA for example are known, they are indeed reactions implemented for surfaces which are already used for biological analysis, especially for Costar surfaces, Nunc surfaces or micro-beads such as Estapor, Bang and Dynal for example, on which molecules of biological interest, DNA, RNA, PNA, proteins or antibodies for example, are anchored.

In the case where the exposed group is a —CH=CH$_2$ radical which is called hereinafter "surface C=C" or "surface with ethylenic bond", no document exists which mentions direct anchoring, in particular of DNA or of proteins.

Within the framework of the present invention, it has been demonstrated that these surfaces have a highly pH-dependent reactivity. This characteristic makes it possible to anchor the nucleic acids or the proteins using pH regions and often with a reaction rate which can be controlled by the pH.

The anchoring of DNA can be carried out by its end onto a surface having groups with ethylenic double bonds, by bringing the DNA into contact with the surface at a pH of less than 8.

In particular, the reaction is carried out at a pH of between 5 and 6, and is then stopped at pH 8.

Thus, for DNA at pH 5.5, the anchoring reaction is complete in one hour (if it is not limited by diffusion) and occurs via the ends. At pH 8 on the other hand, the attachment is very low (reaction rate of 5 to 6 orders of magnitude smaller). This pH dependent attachment effect specific for the ends is an improvement compared with the other surfaces which require functionalization of the DNA (biotin, DIG, NHS, and the like) or specific reagents (carbodiimide, dimethyl pimelidate) which form a peptide or phosphorimide linkage between —NH$_2$ and —COOH or —POOH.

It is also possible to carry out the anchoring of DNA by adsorption of its ends alone onto a surface coated with polylysine or a silane group ending with an amine group.

In order to carry out the anchoring of the DNA by its end on a surface coated with an amine group, the DNA is brought into contact with the surface at a pH of between 8 and 10.

Likewise, it is possible to carry out the anchoring of DNA by its end onto a glass surface treated beforehand in an acid bath, by bringing the DNA into contact with the said surface at a pH of between 5 and 8.

It goes without saying that the present invention involves, in the same spirit, the optionally pH-dependent attachment of all macromolecules of biological interest.

Likewise, these surfaces can anchor proteins directly (protein A, anti-DIG, antibodies, streptavidin and the like). It has been observed that (i) the activity of the molecule can be preserved and (ii) that the reactivity of the prepared surface (initially C=C) is completely overshadowed in favor of the sole reactivity of the molecule of interest. It is therefore possible, starting with a relatively high initial reactivity, to pass to a surface having a very highly specific reactivity, for example that of specific sites on a protein.

By anchoring a specific antibody on the surface (for example anti-DIG), a surface is created whose reactivity is limited to the antigen (for example the DIG group). This indicates that the initial chemical groups are all occulted by the antibodies grafted.

It is also possible to graft onto the reactive (chemically or biochemically) surfaces other molecules with biological activity, especially viruses or other components: membranes, membrane receptors, polysaccharides, PNA, in particular.

It is also possible to attach the product of a reaction of biological interest (for example PCR) onto the prepared surfaces.

The process according to the present invention allows the detection and/or the quantification of biological molecules, but also the measurement of intramolecular distance, the separation of certain biological molecules, especially a sample using antigen/antibody and/or DNA/RNA coupling techniques.

In particular, the subject of the present invention is a process for detecting a macromolecule, consisting of a DNA sequence or a protein in a sample, according to the present invention, characterized in that:

the sample corresponding to solvent A, in which the said macromolecule is in solution, is brought into contact with the surface of the support under conditions for forming a DNA/DNA, DNA/RNA hybrid or for forming the protein/protein reaction product, the hybrid or a macromolecule for labeling the hybrid or the reaction product being anchored in one part, the remainder being free in solution, it is stretched by the movement of the meniscus created by the contact between the solvent and the surface in order to orientate the hybrids or the said labeling macromolecules and the measurement or the observation of the hybrids or of the said labeling macromolecules thus orientated is carried out.

Advantageously, the attached DNA and the DNA of the sample are colored differently and after stretching, the position of the complementary sequence relative to the end of the sample DNA is measured.

Appropriately, the ELISA or FISH detection methods can be used.

The DNA sample may be the product or the substrate of a DNA enzymatic amplification such as PCR, that is to say that the amplification of the DNA can be carried out once it has been anchored and aligned according to the process of the invention or before its anchoring or its alignment.

The passage of the meniscus, by stretching the molecules linearly, in the form of rods, renders them more easily detectable if they are labeled. Moreover, these elongated molecules are stable to the open air and can be observed even after several months, without showing apparent degradation.

During a rehydration, the DNA molecules can remain adsorbed and elongated. Furthermore, it is possible to carry out a hybridization on the elongated molecule.

Furthermore, exhibiting a signal which is correlated and of uniform orientation by virtue of their stretching, these molecules are distinct from the surrounding noise. It is therefore easy to ignore the dusts, the inhomogeneities, which have no special spatial correlation. The alignment is also important because in solution, the molecules in the form of a random coil fluctuate thermally, thereby causing very high variations in their fluorescence signal gathered preferably with a small depth of field and limits their observation. The present invention therefore allows the observation of isolated molecules with a very high signal to noise (S/N) ratio.

It is remarkable that this ratio is independent of the number of molecules anchored. The S/N ratio posed by the detection of one molecule is the same as that for 10,000. Furthermore, this stretching technique makes it possible to easily discriminate between molecules of varying lengths.

It is advantageously possible to proceed to the following stages in order to further improve the S/N ratio:

The molecule being stationary, its fluorescence signal can be integrated.

Microscopic observation presents a reduced field (typically 100 $\mu$m×100 $\mu$m with a ×100 immersion lens, N.A.=1.25). For a 1 $cm^2$ sample, scanning can be carried out, or it is possible to envisage the use of lower magnification lenses (×10 or ×20) but with a high numerical aperture.

The rods being always parallel, it is possible to envisage an optical spatial filtration method in order further to increase the S/N ratio.

Other global fluorescence methods can be envisaged such as those described in European Patent Application EP 103426.

The linearization of the molecules is observed both within the framework of a physicochemical anchoring and in the case of immunological type linkages (DIG/anti-DIG).

Once the surface is in the open air, the DNA molecules are stable (they maintain their integrity even after several weeks) and fluorescent. This property can be advantageously used in order to defer the anchoring stage and the locating/counting stage for the molecules anchored, if this detection is done for example, but without being limited thereto, by fluorescence microscopy. Such a use is covered by the present invention.

A double (or multi) fluorescence technique can possibly be used to improve the S/N ratio or to detect a double functionality.

The stretched molecules can be revealed by various enzymological methods or other methods, such as fluorescence, or the use of radioactive or nonradioactive probes. Their detection can be achieved by measuring a global signal (for example the fluorescence) or by individual observation of the molecules by optical fluorescence microscopy, electron microscopy, local probe methods (STM, AFM and the like).

Thus in general, the present invention allows the detection, separation and/or assay of a molecule in a sample, by a process characterized in that a surface capable of specifically attaching the said molecule is used, and in that the detection, separation or assay are carried out using a reagent, fluorescent or otherwise, which detects the presence of the attached molecule.

Among the reagents, there are fluorescent reagents and nonfluorescent reagents.

The fluorescent reagents contain fluorescent molecules, advantageously chosen to be long molecules of size greater than 0.1 μm and reacting specifically, directly or indirectly, with the pretreated surfaces. For example, but with no limitation being implied, a double-stranded DNA molecule stained by means of fluorescent probes (ethidium bromide, YOYO, fluorescent nucleotides and the like) capable of anchoring directly via one or more ends on a surface optionally having a vinyl or amine type group and the like, especially by a judicious choice of the pH or of the ionic content of the medium or by application of an electric voltage over the surface.

It is also possible to use a special functionalization of the molecule (DIG, biotin and the like) in order to anchor it at one or more points on a surface having complementary sites (anti-DIG, streptavidin and the like).

Nonfluorescent reagents allowing the detection of molecules previously aligned according to the present invention may consist especially of beads or micro-particles anchored via another molecule attached specifically, directly or indirectly, to the aligned molecule and having only a weak nonspecific interaction with the surface.

For example, there may be mentioned Dynal beads coated with streptavidin permitting anchoring on biotinylated DNA aligned according to the present invention.

Depending on whether the desired molecule is detected directly by fluorescence or indirectly by means of the above reagents, the detection will be described as "direct detection" or "flag detection".

In order to limit the problems associated with too slow reaction times, the diffusion times of the reagents towards the surface can be advantageously reduced using small reaction volumes. For example, but with no limitation being implied, by carrying out the reaction in a volume of a few microliters determined by the space between two surfaces of which one is treated so as to have reactive sites and the other is inert or treated so as not to have reactive sites, under the reaction conditions.

The detection of the number of aligned molecules can be carried out on a small number of molecules (typically 1 to 1000), by a low-noise macroscopic physical test requiring neither electron microscope nor radioactivity nor necessarily PCR.

The alignment and detection processes according to the present invention are capable of being carried out by persons having only limited laboratory experience.

The specificity of certain biological reactions may be limited. Thus, within the framework of the hybridization, the hybrids may be imperfect (reactions with other sites) while having a reduced number of pairing and therefore a lower quality of binding. The present invention also covers the possible use of a stage for testing the quality of the bonds obtained. This test makes it possible to dissociate the products weakly and nonspecifically paired by adsorption, hydrophobic forces, imperfect hydrogen bonds, imperfect hybridization, in particular.

Accordingly, the invention also relates, in a detection or assay process as described above, to a process where the product of the reaction between the molecule with biological activity and the sample molecule is subjected to a stress in order to destroy the mismatches before the detection.

This process offers, in addition to the possibility of destroying the mismatched pairs, the possibility of orientating the products of the coupling, which facilitates the measurements or the observations.

It is thus possible to apply to the surfaces, after attachment of the complementary elements, a stress which may consist of the single or combined use of:

centrifugation, gradient of magnetic field applied to the nonfluorescent reagents taken, in this case, to include magnetizable or magnetic microbeads, stirring, liquid flow, meniscus passage, electrophoresis temperature variation, and/or temperature gradient.

The number of systems to have remained intact or to have been destroyed is then determined by the low-noise detection techniques described above.

The alignment and detection techniques described according to the present invention can be used for numerous applications among which, but with no limitation being implied:

the identification of one or more elements of DNA or RNA sequence which can be advantageously used for the diagnosis of pathogens or the physical map of a genome. In particular, the techniques described above make it possible to obtain a physical map directly on genomic DNA without the intermediate use of a cloning stage. It is understood that the combed molecule having been stretched relative to its crystallographic lengths, relative measurements are carried out. It is thus possible to measure the size of the DNA fragments and the distance between fragments, with a resolution of the order of 200 nm for optical methods or of the order of 1 nm by the use of near field methods such as AFM or STM in order to visualize and measure the distance between probes on the aligned DNA.

This naturally leads to:

1) the detection of deletions, additions or translocations of genomic sequences, in particular in the diagnosis of genetic diseases (for example Duchenne's myopathy);
2) the identification of promoters of various genes by measuring the distance between the regulatory sequences and those expressed;
3) the localization of regulatory proteins by identifying their position along the DNA or the position of their target sequence;
4) the partial or complete sequencing by measuring the distance using near field microscopy (for example AFM or STM) between hybridized probes belonging to a base oligonucleotide of given length;

the enzymatic amplification in situ on aligned DNAs;

the improvement of the sensitivity of ELISA techniques with the possibility of detecting a small number (possibly less than 1000) of immunological reactions.

Thus, physical mapping can be carried out directly on a genomic DNA without the intermediate use of a cloning stage. The genomic DNA is extracted, purified optionally cleaved with one or more restriction enzymes and then combed on surfaces according to the process of the present invention.

The position and size of the desired gene on the genomic DNA are then determined by hybridization with probes specific for the said gene, especially extracted from parts of the complementary DNA (cDNA) of the product of the said desired gene.

Similarly, by hybridizing a genomic DNA combed, then denatured with total cDNA labeled by fluorescence or any other marker allowing the hybrid to be localized, the position, size and number of exons of the gene in question are identified and its size and its genetic organization (exons, introns, regulatory sequences) are deduced therefrom.

The position of the gene having been determined as described above or being known, it is then possible to identify, by hybridization, the flanking sequences of the gene. For that, the procedure is advantageously carried out by hybridization with labeled probes, obtained for example from an oligonucloetide library, in order to identify two or more probes which hybridize on either side of the gene.

From this determination, it is then possible, by enzymatic amplification techniques, for example in situ PCR (Nuovo G. J. PCR in situ hybridization: protocols and applications, Raven Press (1992)) to amplify the fragment delimited by the flanking probes which can serve as primers for the reaction, which fragment may contain the desired gene with its regulatory regions which may be tissue- or development-specific and which can then be isolated and purified.

The procedure can also be carried out by in situ polymerization on primers extracted from the cDNA of the gene in question in order to extract DNA fragments complementary to the flanking regions of the gene as mentioned by Mortimer et al. (Yeast 5, 321, 1989). These fragments can then serve in the preparation of primers for a process of enzymatic amplification of the gene and of its flanking sequences.

The methods cited by A. Thierry and B. Dujon (Nucl. Acid Research 20 5625 (1992)) for inserting, by homologous recombination or randomly, known endonuclease-specific sites into a genomic DNA or a genomic DNA fragment, may also be used. The combing of this DNA allows the identification of the gene of interest and of the specific sites inserted, by the in situ hybridization methods described above. From this identification and preferably, if the sites of interest are regions of interest which are close to the gene, they will be used as primer for a reaction of enzymatic amplification (in situ and the like) of the gene in question and of its flanking sequences.

The amplification of the desired gene then proceeds using known enzymatic amplification techniques such as PCR on the amplified fragment as described above, using primers which can be reached by the exons constituting the cDNA, or primers corresponding to flanking sequences.

By the combing of genomic DNA and the like, it is also possible to determine, by hybridization, the presence or the absence of regulatory sequences of a specific proximal gene, from which the possible families of proteins for regulating this gene (for example: helix-loop-helix, zinc-finger, leucine-zipper) will be determined.

The specific reactions between particular DNA/RNA/PNA sequences and another molecule (DNA, RNA, protein) can occur before or after aligning the molecules according to the present invention.

Thus, in the field of genetic diagnosis and physical mapping, the known methods of FISH (Pinkel et al., Proc. Nat. Acad. Sci. USA 83, 2934 (1986)) are advantageously used to hybridize single-stranded oligonucleotides labeled with DNA first aligned, and then denatured. The revealing of the hybrids will be carried out using known techniques (fluorescence, microbeads and the like) with a resolution in the measurement of the distances ranging from 0.2 $\mu$m (optically) to 1 nm (by near field microscopy; AFM, STM and the like).

Alternatively, it is possible to first hybridize fluorescent marker DNAs with single-stranded DNA in solution, and then to align this construct by action of the meniscus after having converted it to double-stranded DNA and anchored it on an appropriate surface.

It is also possible to use the present invention for detecting the presence of a pathogen. By way of example, the procedure can be carried out in two different ways depending on whether the recognition reaction (hybridization, attachment of proteins) occurs before or after alignment by the meniscus.

Thus, by way of example, one or several oligonucleotide probes are anchored in one or more regions of a surface. The hybridization of the potentially pathogenic DNA is carried out in situ under stringent conditions so as to anchor only the hybridized molecules. Their detection and quantification is carried out after alignment by the meniscus according to the present invention.

Alternatively, the potentially pathogenic DNA is first aligned, then denatured and hybridized with an oligonucleotide probe under stringent conditions. The detection of the hybrid is then carried out by known methods, especially by the FISH method, as described above.

Similarly, it is possible to detect the presence (or the absence) of a small number of molecules, such as proteins, lipids, sugars or antigens. A minor modification of the ELISA techniques will be advantageously carried out, the usual detection method being replaced by the detection of a fluorescent molecule aligned according to the present invention and coupled to one of the reagents of the ELISA reaction.

Moreover, as mentioned by K. R. Allan et al. (US 84 114), Genetic mapping can be carried out by measuring the size of the DNA fragments. Now, the novel techniques for stretching molecules described above (stretching by meniscus) allows the length of the stretched molecules to be measured, and this on a very small sample (a few thousandths of molecules).

It is for example possible, but with no limitation being implied, to carry out the procedure in the following manner:

A DNA sample is fragmented (by means of restriction enzymes) stained with a fluorophore and then anchored on a surface. The molecules are then stretched by the meniscus and the size of the stretched fragments is determined by optical fluorescence microscopy with a resolution and a maximum size of the order of 1000 bp (0.3 $\mu$m).

For this purpose, but also if it is desired to align very long molecules ($\geq 10$ $\mu$m), known techniques will be advantageously used in order to limit the degradation of long macromolecules during their handling (by hydrodynamic shearing).

Thus, as mentioned by D. C. Schwartz, condensation of the molecules will be advantageously carried out by means of a condensing agent (for example spermine or an alcohol) during their handling. Optionally, their decondensing will occur during contact between the solvent A and the anchoring surface S.

In order to reduce the degradation of the macromolecules during stretching by the meniscus, meniscus translation techniques will be used which minimize hydrodynamic shearing. For example, but with no limitation being implied, by very slowly removing ($\leq 200$ $\mu$/sec) the surface S from a substantial volume ($\geq 100$ $\mu$l) of the solvent A.

The subject of the present invention is also a surface having one or more types of aligned macromolecules obtained according to the present invention. In particular, it is possible to obtain a surface or a stack of surfaces having anisotropic optical or electrical properties.

The subject of the present invention is also a process for aligning and detecting DNA in which the DNA is stretched by an aligning process according to the invention, then denatured and hybridized with specific probes in order to determine the position or the size of one or more specific sequences.

The subject of the present invention is also a process for the physical mapping of a gene on a genomic DNA in which the DNA is aligned or detected according to a process of the invention.

In particular, the position and the size of the desired gene on the genomic DNA are determined by hybridization with probes specific for the said gene to be mapped.

A subject of the present invention is also
- a kit useful for carrying out a mapping process according to the invention, consisting of total genomic DNA from a reference host,
- a support having a surface permitting the anchoring and the alignment of the patient's DNA in accordance with the process of the invention
- probes specific for the gene(s) to be mapped and reagents for the hybridization and the detection of the DNA.

The subject of the present invention is also a process for aligning and detecting DNA in which the DNA is stretched, then denatured and hybridized with specific probes in order to determine the presence or the absence of one or more DNA sequences in the said aligned DNA.

The present invention allows the implementation of a process for the diagnosis of a pathology related to the presence or the absence of a DNA sequence specific for the pathology in which an alignment process according to the invention is used.

The subject of the present invention is also a kit useful for carrying out a diagnostic process according to the invention, characterized in that it contains a support whose surface permits the anchoring and the alignment of the patient's DNA according to a process of the invention, probes specific for the gene involved in the sought pathology and reagents for the hybridization and the detection of the DNA.

The subject of the present invention is also a kit useful for carrying out a diagnostic process according to the invention, characterized in that it contains a support whose surface has probes specific for the gene involved in a pathology, in particular optionally labeled pathogenic DNA, which are aligned according to the process of the present invention and optionally denatured; the reagents for preparing and labeling the patient's DNA for its hybridization (for example photobiotin, nick translation or random priming kit) and reagents for the hybridization and the detection of the DNA according to the in situ hybridization techniques as described above.

It is understood that combed probes relating to different pathogens may be present on different supports or on the same support. The identification of the corresponding pathogen can be carried out after hybridization, either spatially (the different probes are spatially separated for example by photochemical anchoring before their combing) or by a difference in the fluorescence spectrum of the different hybrids, resulting from a prior differential labeling of the probes.

Finally, the subject of the present invention is a process for preparing a gene in which the position of the said gene on the genomic DNA aligned by the process according to the invention is identified by means of a probe specific for the said gene, the sequence of the said gene and optionally its flanking sequences are amplified by enzymatic amplification, in particular by in situ PCR.

The present invention therefore makes it possible to carry out a process for replacing a gene in the genome of an eukaryotic cell by targeted insertion of a foreign gene by means of a vector containing the said foreign gene prepared according to the above gene preparation process.

The targeted insertion can be carried out according to the techniques described in WO90/11354 by transfecting eukaryotic cells with a vector containing the said foreign DNA to be inserted flanked by two genomic sequences which are contiguous to the desired site of insertion in the recipient gene. The insert DNA may contain either a coding sequence, or a regulatory sequence. The flanking sequences are chosen so as to allow, by homologous recombination, depending on the case, either the expression of the coding sequence of the insert DNA under the control of the regulatory sequences of the recipient gene, or the expression of a coding sequence of the recipient gene under the control of a regulatory sequence of the insert DNA.

The genomic genes and the cDNAs obtained using the process for localizing genes according to the invention can be inserted into expression vectors capable of being inserted into a prokaryotic, eukaryotic or viral host cell. The derived proteins, polypeptides and peptides are included in the present invention.

In the "diagnostic" mode, the probes (the "anchors") possess a reactive group (DIG, biotin and the like) capable of anchoring specifically on a surface according to the present invention (having for example as anchoring site an anti-DIG antibody or streptavidin). The detection of the anchoring reaction can be carried out directly by detection of the fluorescence of the DNA molecule stained by fluorescent molecules (ethidium bromide, YOYO, fluorescent nucleotides) (FIG. 1). It can also be carried out indirectly by detection of a "flag molecule": a reagent capable of attaching to the DNA/RNA molecule (for example by hybridization, protein-DNA interaction and the like), but having no affinity for the anchoring sites of the probe.

In the "mapping" mode, in situ hybridization techniques (FISH) can be used. It is also possible to envisage other techniques, for example by hybridizing in solution DNA with probes having fluorescent reagents according to the present invention. The detection of the position of the probes is carried out after aligning the molecule according to the present invention.

EXAMPLE 1

Materials and Methods

The λ DNA and the monoclonal antibody (anti-DIG) are obtained from Boehringer-Mannheim. The trichlorosilanes are obtained from Roth-Sochiel. The fluorescent nucleic probes (YOYO1, YOYO3 and POPO1) are obtained from Molecular Probes. The ultraclean glass cover slips are obtained from Erie Scientific (ESCO) cover slips). The magnetic particles are obtained from Dynal. The microscope is a Diaphot inverted microscope from NIKKON, equipped with a Xenon lamp for epifluorescence and a Hamamatsu intensified CCD camera for the visualization.

Surface Treatment

Glass cover slips are cleaned for one hour by UV irradiation under an oxygen atmosphere (by formation of ozone). They are then immediately placed in a desiccator previously purged of traces of water by an argon stream. A volume of about 100 to 500 µl of the appropriate trichlorosilane ($H_2C=CH-(CH_2)_N-SiCl_3$ is introduced into the desiccator, from which the surfaces are removed after about 12 hours (n=6) or 1 hour (n=1). Upon taking out, the surfaces are clean and nonwetting.

The functional groups of these double bond surfaces ($H_2C=CH-$) can be converted to carboxyl groups (—COOH) by soaking the treated cover slips, as described above, for about ten minutes in a solution of 25 mg $KMnO_4$, 750 mg $NaIO_4$ in 1 l of water, then by rinsing them three times in ultrapure water.

The cover slips thus functionalized can react with proteins. A volume of 300 µl of an aqueous solution (20 µg/ml) of proteins (protein A, streptavidin and the like) is deposited on a cover slip functionalized with a ($H_2C$=CH—) group. This cover slip is incubated for about two hours at room temperature, then rinsed three times in ultrapure water. The surfaces thus treated are clean and wetting. The surfaces treated with protein A can then react with an antibody, for example an anti-DIG antibody, by incubating in a solution of 20 µg/ml of antibody.

Moreover, on the surfaces having carboxyl groups, it is possible to graft oligonucleotides having an amine end (—$NH_2$), 200 µl of a solution of MES (50 mM, pH 55), carbodiimide (1 mg/ml) and 5 µl of amino-oligo-nucleotide (10 pmol/140 µl) are deposited on a carboxylated surface and incubated for about 8 hours at room temperature. The cover slip is finally rinsed three times in NaOH (0.4 M) and then four times in ultrapure water. The cover slips thus prepared can hybridize DNAs complementary to the anchored oligonucleotide.

Anchoring of Native DNA on a Double Bond Surface

A drop of 2 µl of a fluorescence-labeled λ DNA (YOYO1, POPO1 or YOYO3, but with no specific end labeling) of varying concentration and in different buffers (total number of molecules <$10^7$) is deposited on a pretreated cover slip (C=C) and covered with an untreated glass cover slip (diameter 18 mm). The preparation is incubated for about 1 hour at room temperature in an atmosphere saturated with water vapor. In a 0.05 M MES buffer (pH=5.5), a virtually general anchoring of the DNA molecules is observed. In contrast, in a 0.01 M Tris buffer (pH=8), there is practically no anchored molecule (ratio>$10^6$). This dependence can make it possible to control the activation/deactivation of surfaces (with respect to DNA) via the pH.

The action of the meniscus on the molecule is limited to its immediate vicinity. The part of the molecule in solution in front of the meniscus fluctuates freely and the part left stuck on the surface behind the meniscus is insensitive to a change in the direction of the meniscus. The extension rate of the molecule is therefore uniform and independent of its size.

Alignment and Detection of the Anchoring by the Action of the Meniscus

By transferring the preceding preparation to a dry atmosphere, the solution, upon evaporating, will stretch the DNA molecules anchored on the surface, perpendicularly to the meniscus. The capillary force on the DNA molecule (a few tens of picoNewtons) is indeed sufficient to completely stretch the molecule (greater than the entropic elasticity forces), but too weak to break the bond between the end of the molecule and the treated surface. The DNA having been fluorescence labeled, the stretched molecules (total length about 22 µm) can be individually and easily observed. The anchoring between the surface and the DNA being limited to the ends, it is possible to stretch either DNA of λ phage, of YAC or of E. coli (total length greater than 400 µm). This DNA preparation, stretched, fluorescent and in the open air, is stable for several days and can be observed in a nondestructive manner, by epifluorescence (Nikkon Diaphot inverted microscope with a ×100 lens, O.N.: 1.25).

Specific Anchoring and Detection

By treating the surfaces as described above with a specific monoclonal antibody, it is possible to control their specificity very precisely. Thus, the specificity of anti-DIG treated surfaces was tested in relation to λ DNA hybridized with an oligonucleotide complementary to one of the Cos ends and possessing a digoxigenin group (DIG) and in relation to nonhybridized DNA. In the first case, a virtually general extension of the anchored molecules, by the action of the meniscus, was observed. In the second case, only a few anchored DNA molecules (<10) were observed in the whole sample. It is therefore estimated that the specificity of the method according to the invention is greater than $10^6$.

λ DNAs were also hybridized with oligonucleotides complementary to one of the COS ends and attached to carboxylated surfaces, as described above. The hybridization conditions (pure water at 40° C.) were not stringent because under stringent conditions (high salinity) the fluorescence of the YOYO1 probes disappears and the hybridized DNAs cannot be seen. It was also possible to align the DNAs thus hybridized by passage of the meniscus.

Sensitivity of the Detection

In order to determine the sensitivity of the detection method by extension of the meniscus, 2.5 µl drops of a solution of λ DNA in 0.05 M MES (pH=5.5) containing a total of $10^5$, $10^4$ and 1000 molecules, were deposited on double bond surfaces. The anchoring and the alignment are carried out as described above. The cover slips are then observed by epifluorescence microscopy to determine the density of combed molecules. The latter indeed corresponds to that estimated: about 4–6 DNA molecules per field of vision (100 µm×100 µm) for a total of $10^5$ DNA molecules. For the lowest concentration, it was possible to observe about ten molecules extended by the action of the meniscus. This number is essentially limited by the large number of fields of vision required to cover the whole sample (about 25,000), which makes a manual search difficult, but it can be advantageously carried out automatically or also with a weaker lens, but with a larger field. In conclusion, the sensitivity of the method according to the invention allows detection and individual counting of less than 1000 DNA molecules.

Dependence of the Stretching on the Surface Treatment

Figure 7A:
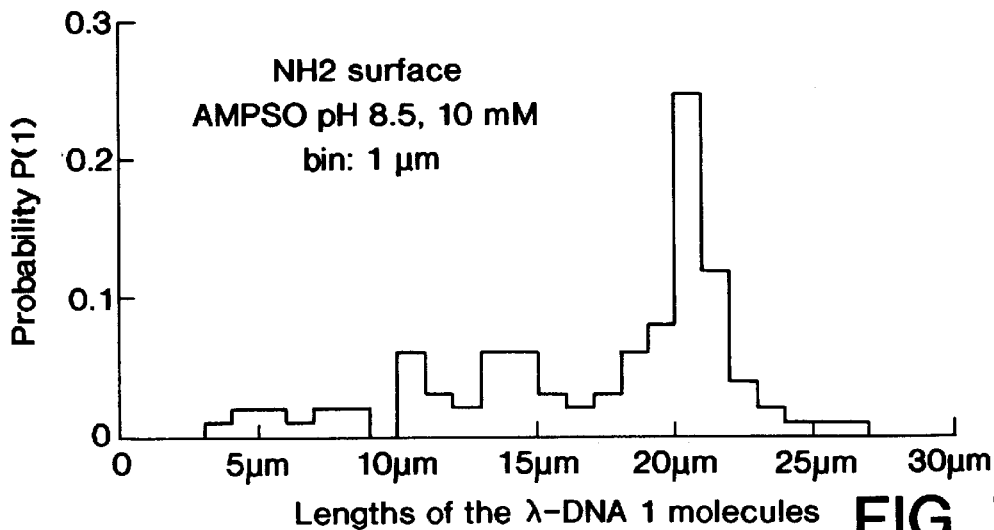
FIG. 7 contains histograms of the length of the combed λ DNA molecules on glass surfaces:
   a) coated with silane molecules ending with an amine group,
   b) coated with polylysine,
   c) cleaned in a hydrogen peroxide/sulfuric acid mixture.
Figure 7B:
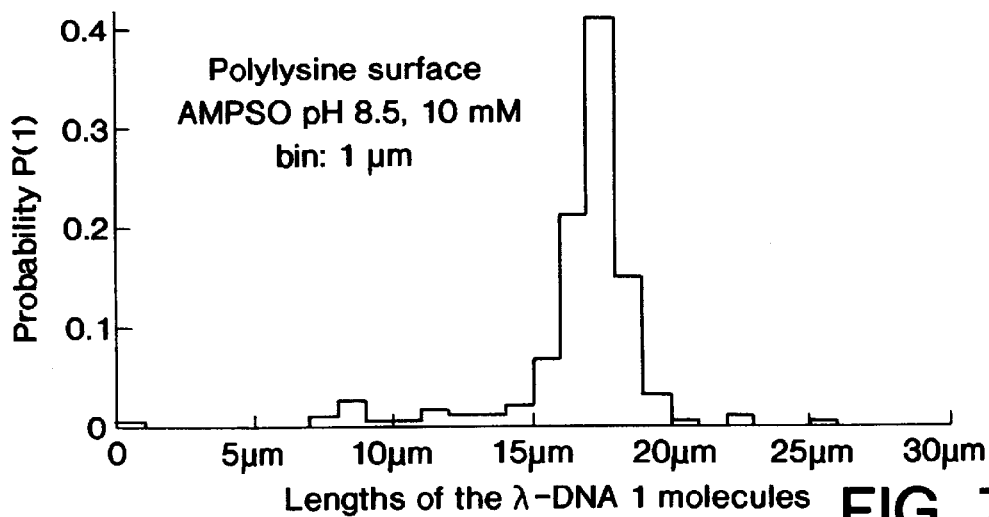
Figure 7C:
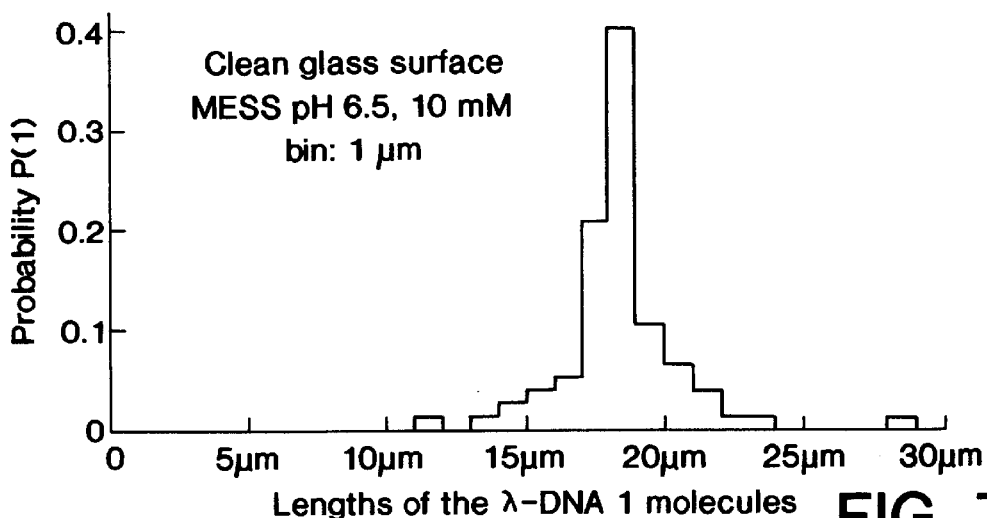

The histogram of the lengths of λ DNA grafted on different surfaces and then aligned by passage of the meniscus shows a well defined peak but which is different for the different surfaces. Thus, on surfaces coated with a silane which end with a vinyl group, the DNA is stretched up to about 22 µm (see above) for surfaces silanized with an amine group (—$NH_2$), the histogram has a peak at 21 µm (FIG. 7(a)) and on clean glass at about 18.5 µm (FIG. 7(c)).

The stretching therefore depends on the surface treatment.

EXAMPLE 2

Combing of DNA Molecules on Different Surfaces

The molecular combing of DNA on glass surfaces treated in various ways was observed. Advantage is taken of the difference in adsorption between the ends of the molecule and the rest of the molecule. By adsorbing positively charged polymers onto a glass surface, adsorption of negatively charged DNA molecules is enhanced, however when this charge is large, the DNA molecule is stuck over its entire length and the combing is impossible. However, it is possible to modify the charge of the polymers adsorbed on the glass by modifying the pH conditions, indeed, the positive charges are carried for example by the $NH_2$ groups which pass to the protonated state $NH_3^+$ for a pH below the pK of the corresponding base. In basic pH, the charges disappear and the surface no longer attracts DNA. By finely controlling the pH, it was observed that the DNA molecules in solution passed from a state where they are completely stuck to the surface to an intermediate phase where they are anchored only by their ends and then to a phase where the surface no longer has affinity for the DNA. In the intermediate phase, molecular combing can be carried out.

Surfaces coated with a silane ending with an $NH_2$ group were studied for which there is observed complete sticking at pH<8, and combing for 8.5<pH<9.5. The number of combed molecules is maximum at pH=8.5 it is divided by 2 at pH=9 and by 4 at pH=9.5. Also the relative extension on this surface which corresponds to 1.26 was determined as can be seen in histogram 2 of FIG. 7 which represents histograms of the length of the combed λ DNA molecules on glass surfaces:

a) coated with silane ending with an amine group, b) coated with polylysine, c) cleaned in a hydrogen peroxide/sulfuric acid mixture.

Figure 8:
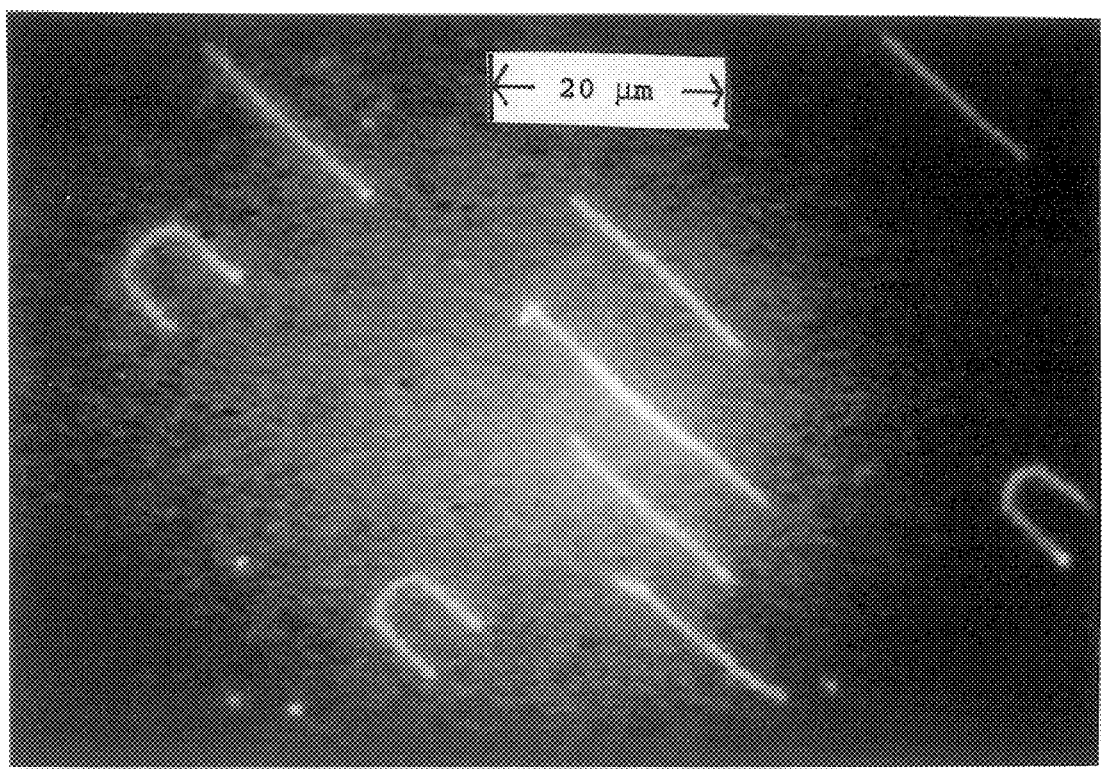
FIG. 8 represents combed DNA molecules on glass surfaces coated with polylysine. It can be noted that the molecules attached by their two ends form loops.

Surfaces coated with polylysine were also examined and found to exhibit similar attachment characteristics as regards the pH: combing region 8.5 and exhibiting a shorter relative extension: 1.08. A typical example can be obtained in FIG. 8 which represents combed DNA molecules on glass surfaces coated with polylysine. It can be observed that the molecules attached by their two ends form loops.

Finally, the same behavior was found on glass surfaces freshly cleaned in a hydrogen peroxide/concentrated sulfuric acid mixture. These surfaces are highly wetting and become rapidly contaminated; however, a combing region was observed between 5.5<pH<7.4 whereas the region of strong adsorption is situated at pH=4.5. The relative extension of the molecules corresponds to 1.12.

EXAMPLE 3
Uniform and Directional Alignment of YAC

Figure 9:
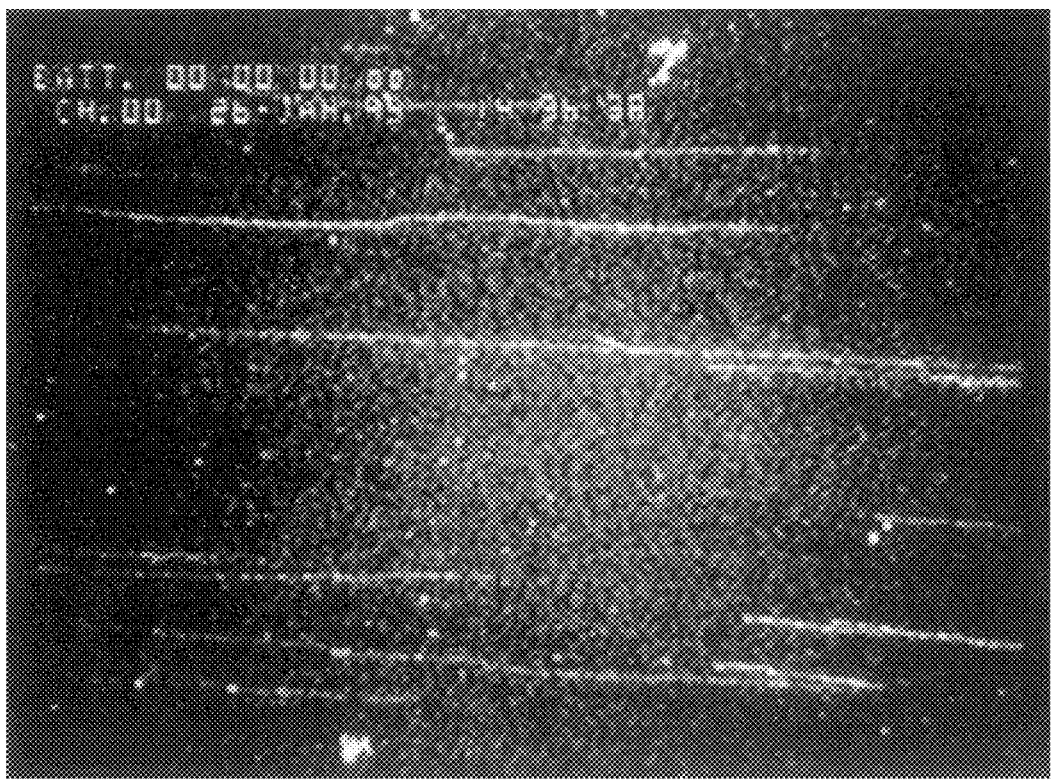
FIG. 9 represents YACs combed by removal of a treated cover slip in a solution of these molecules.

1 µg of YAC previously stained in its agarose plug by means of a YOYO1 fluorescent probe is heated to 68° C., agarased and then diluted in 10 ml of MES (50 mM pH 5.5). Two silanized cover slips (C=C surfaces) are incubated for ≈1.5 h in this solution and then removed at about 170 µm/sec. The YAC molecules are all aligned parallel to the direction of removal of the cover slips (FIG. 9). The integrity of the molecules thus aligned is better than by evaporation after deposition between two cover slips.

Hybridization of a Cosmid with a Combed YAC

A YAC stained as previously described is anchored on a C=C surface (between two cover slips) and then aligned by the meniscus, during evaporation of the solution. The probes (cosmids) are labeled by incorporation of a biotinylated nucleotide by the randon priming technique. The labeled probes (100 ng) and 5 µg of sonicated salmon sperm DNA (≈500 bps) are purified by precipitation in Na-acetate and ethanol, and then denatured in formamide.

The combed YACs are denatured between two cover slips with 120 µl of denaturing solution (70% formamide, 2×SSC) on a hotplate at 80° C. for 3 minutes. The previously denatured probes (20 ng) are deposited on the cover slip in a hybridization solution (55% formamide 2×SSC, 10% dextran sulfate) covered with a cover slip which is sealed with rubber cement. The hybridization is carried out overnight at 37° C. in a humid chamber.

The detection of the hybrids is performed according to procedures known for in situ hybridizations on decondensed chromosomes (D. Pinkel et al., PNAS USA 83, 2934 (1986) and PNAS USA 85, 9138 (1988)).

Figure 10:
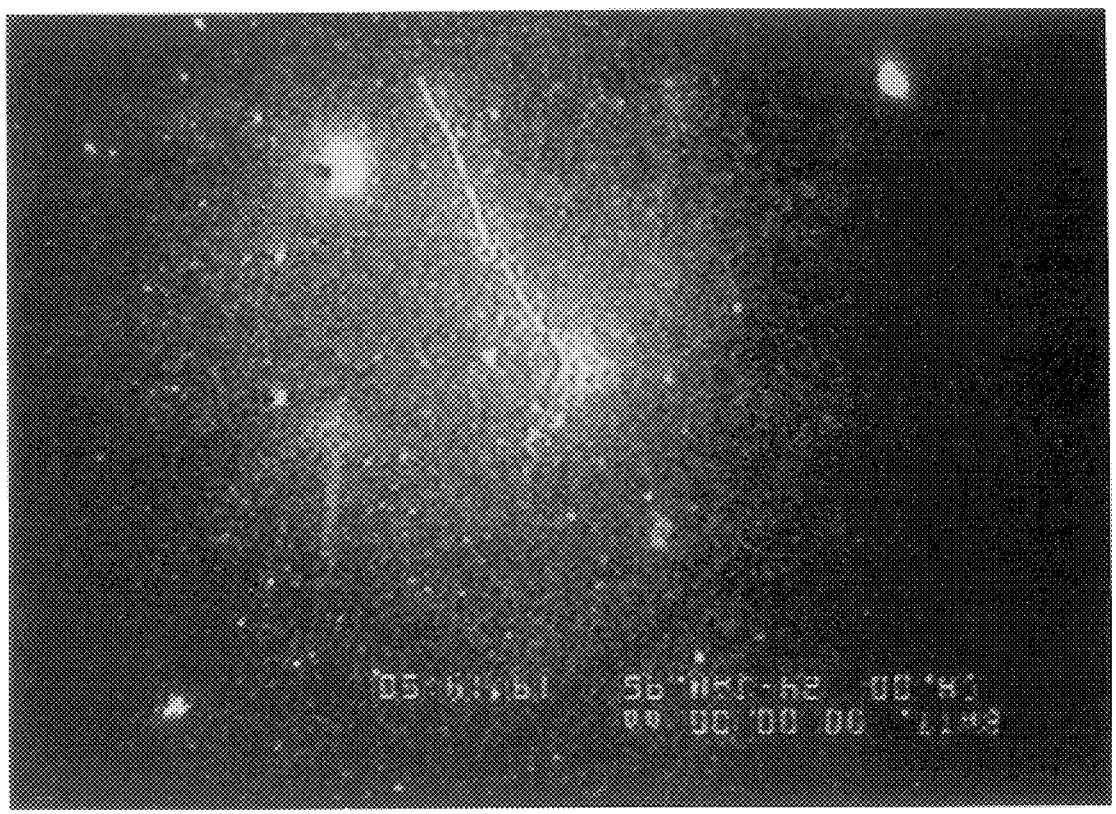
FIG. 10 shows the identification of the presence and the size of a cosmid on a YAC by in situ hybridization.

Hybridized segments such as that shown in FIG. 10 are then observed by fluorescence microscopy. This example demonstrates the possibility of detecting the presence of a gene on a DNA molecule, which can be used for diagnostic purposes or for physical mapping of the genome.

What is claimed is:

1. A process for aligning a nucleic acid on a surface S of a support, wherein the process comprises:

(a) providing a support having a surface S;

(b) contacting the surface S with the nucleic acid;

(c) anchoring the nucleic acid to the surface S;

(d) contacting the surface S with a first solvent A;

(e) contacting the first solvent A with a medium B to form an A/B interface, wherein said medium B is a gas or a second solvent;

(f) forming a triple line S/A/B (meniscus) resulting from the contact between the first solvent A, the surface S, and the medium B; and (g) moving the meniscus to align the nucleic acid on the surface.

2. A process according to claim 1, wherein the movement of the meniscus is achieved by evaporation of the solvent A.

3. A process according to claim 1, wherein the movement of the meniscus is achieved by movement of the A/B interface relative to the surface S.

4. A process according to claim 3, wherein the surface S is removed from the solvent A or the solvent A is removed from the surface S in order to move the meniscus.

5. A process according to claim 1 wherein the meniscus is a water/air meniscus.

6. A process according to claim 1 wherein the surface comprises an organic polymer, an inorganic polymer, a metal, a metal oxide, a sulfide, a semiconductor element, or a combination thereof.

7. A process according to claim 1 wherein the surface comprises glass, surface-oxidized silicon, gold, graphite, molybdenum sulfide, or mica.

8. A process according to claim 1 wherein the support comprises a plate, a bead, a fiber, or a particle.

9. A process according to claim 1 wherein the solvent A is placed between the support of surface S and a second support.

10. A process according to claim 1, wherein the anchoring of the nucleic acid is a physicochemical interaction.

11. A process according to claim 1, wherein the surface S of the support comprises an exposed reactive group having an affinity for the nucleic acid or a molecule with biological activity capable of recognizing the nucleic acid.

12. A process according to claim 1 wherein the surface comprises vinyl, amine, carboxyl, aldehyde, or hydroxyl groups.

13. A process according to claim 11, wherein the surface S of the support comprises: a substantially monomolecular layer of an organic compound having at least:

(a) an attachment group having an affinity for the support; and (b) an exposed group having no or little affinity for the support and the attachment group under attachment conditions, but having an affinity for the nucleic acid or the molecule with biological activity.

14. A process according to claim 11, wherein the anchoring of the nucleic acid to the surface comprises:

(a) contacting the nucleic acid with the exposed reactive group;

(b) adsorbing the nucleic acid to the exposed reactive group at predetermined pH values or ionic content, or by applying an electric voltage.

15. A process according to claim 14, wherein the pH conditions are between a pH resulting in a state of complete adsorption and a pH resulting in an absence of adsorption.

16. A process according to claim 14, wherein the exposed reactive group is an ethylenic double bond or an amine group.

17. A process according to claim 14 wherein the exposed reactive group is a vinyl or amine group.

18. A process according to claim 16, wherein the adsorption of the nucleic acid occurs at an end of the nucleic acid, the exposed reactive group is an ethylenic double bond, and the pH is less than 8.

19. A process according to claim 18, wherein the pH is between 5 and 6.

20. A process according to claim 17, wherein the adsorption of the nucleic acid occurs at an end of the nucleic acid, the surface is a polylysine or a silane group, and the exposed group is an amine group.

21. A process according to claim 17, wherein the adsorption of the nucleic acid occurs at an end of the nucleic acid, the exposed reactive group is an amine group, and the pH is between 9 and 10.

22. A process according to claim 14, wherein the adsorption of the nucleic acid occurs at an end of the nucleic acid, the surface is glass, and the pH is between 5 and 8.

23. The product of the process of one of claims 1, 13, or 14.

24. A process for detecting a nucleic acid in a sample, wherein the process comprises:
   (a) providing a support having a surface S;
   (b) contacting the surface S with a nucleic acid;
   (c) anchoring the nucleic acid to the surface S;
   (d) contacting the surface S with a first solvent A;
   (e) contacting the first solvent A with a medium B, to form an A/B interface, wherein said medium B is a gas or a second solvent;
   (f) forming a triple line S/A/B (meniscus) resulting from the contact between the first solvent A, the surface S, and the medium B;
   (g) moving the meniscus to align the nucleic acid on the surface; and
   (h) detecting, either directly or indirectly, the aligned nucleic acid.

25. A process according to one of claims 1, 13, 14, or 24, wherein the nucleic acid has a sequence complementary to a second nucleic acid sequence in a sample.

26. A process according to one of claims 11 or 13, wherein the molecule with biological activity is biotin, avidin, streptavidin, derivatives thereof, or an antigen-antibody system.

27. A process according to claim 24, wherein the surface exhibits low fluorescence and the nucleic acid is detected, either directly or indirectly, using a fluorescent reagent.

28. A process according to claim 24, wherein the detection is performed using beads.

29. A process according to claim 24, wherein the detection is performed using optical or near field microscopy.

30. A process according to claim 24, further comprising binding a second molecule to the nucleic acid attached to the surface S, and disrupting nonspecific binding.

31. A process for detecting a nucleic acid in a sample, wherein the process comprises:
   (a) providing a support having a surface S;
   (b) anchoring a second nucleic acid to the surface S;
   (c) contacting the surface S with a sample A, the sample A comprising a nucleic acid that binds to the second nucleic acid anchored to the surface in a first solvent;
   (d) binding the nucleic acid in the sample to the anchored nucleic acid;
   (e) contacting the sample A with a medium B to form an A/B interface, wherein said medium B is a gas or a second solvent;
   (f) forming a triple line S/A/B (meniscus) resulting from the contact between the sample A, the surface S, and the medium B;
   (g) moving the meniscus to align the bound nucleic acids on the surface; and
   (h) detecting, either directly or indirectly, the aligned nucleic acids.

32. A process according to one of claims 24 or 31 wherein the method of detecting is ELISA or FISH.

33. A process according to one of claims 24 or 31 wherein the nucleic acid in the sample is the product of an enzymatic amplification.

34. A process for the mapping of genes comprising:
   (a) providing a support having a surface S;
   (b) contacting the surface S with a nucleic acid to be mapped;
   (c) anchoring the nucleic acid to the surface S;
   (d) aligning the anchored nucleic acid on the surface according to claim 1;
   (e) hybridizing a second nucleic acid of known sequence to the first nucleic acid; and
   (f) detecting the hybridization between the first nucleic acid and the second nucleic acid.

35. The process according to claim 34, wherein the first or the second nucleic acid comprises genomic DNA.

36. A process according to claim 34, wherein the position and/or the size of the second nucleic acid, which is bound to the first nucleic acid, is measured.

37. A process according to claim 34, wherein step (d) comprises stretching the anchored nucleic acid.

38. A process according to claim 34, wherein the presence or absence of hybridization provides a diagnosis of a pathology.

39. A kit comprising:
   (a) a support having anchored and aligned nucleotide probes, wherein the probes are specific for a gene associated with a pathology;
   (b) reagents for labeling the probes or a patient's DNA;
   (c) reagents for alignment; and
   (d) reagents for hybridization and detection of the DNA or the probes.

40. A process for amplifying a nucleic acid sequence, wherein the process comprises:
   (a) providing a support having a surface S,
   (b) contacting the surface S with a nucleic acid;
   (c) anchoring the nucleic acid to the surface S;
   (d) contacting the surface S with a first solvent A;
   (e) contacting the first solvent A with a medium B to form an A/B interface, wherein said medium B is a gas or a second solvent;
   (f) forming a triple line S/A/B (meniscus) resulting from the contact between the first solvent A, the surface S, and the medium B;
   (g) moving the meniscus to align the nucleic acid on the surface; and
   (h) performing an enzymatic amplification reaction on the aligned nucleic acid.

41. The process according to claim 40, wherein the product of the enzymatic amplification reaction is cloned into a recombinant vector.

42. A process according to claim 6, wherein the semiconductor element is a silicon, an oxide of a semiconductor element, or a combination thereof.

43. A process according to claim 9, wherein the meniscus is moved by evaporation.

44. A process according to claim 10, wherein the physicochemical interaction is adsorption.

45. A process according to claim 10, wherein the physicochemical interaction is a covalent linkage.

46. A process according to claim 10, wherein the physicochemical interaction is a direct interaction between the surface S and the nucleic acid.

47. A process according to claim 10, wherein the physicochemical interaction is an indirect interaction between the surface S and the nucleic acid.

48. A process according to claim 22, wherein the glass is treated beforehand in an acid bath.

49. A process according to either claim 31 or 34, wherein the nucleic acid attached to the surface and the nucleic acid in the sample are differentially labeled with a fluorescent antibody.

50. A process according to claim 49, wherein the position and/or the size of the nucleic acid in the sample, when bound to the attached nucleic acid, is measured.

51. The process according to claim 41, wherein the recombinant vector comprises a regulatory sequence.

52. The product of the process of claim 31, wherein the product comprises the nucleic acids on the surface.

53. The product of the process of claim 34, wherein the product comprises the hybridized nucleic acids aligned on the surface.

54. A process of one of claims 1, 24, or 31, wherein a molecule with biological activity anchors the nucleic acid to the surface.

55. A process according to claim 54, wherein the molecule with biological activity is a protein, a nucleic acid, a lipid, a polysaccharide, or a derivative thereof.

56. A process according to claim 54, wherein the molecule with biological activity is an antibody, an antigen, a DNA, a RNA, a ligand, a receptor of ligand, or a derivative thereof.

57. A process of claim 54, wherein the molecule with biological activity is biotin, avidin, streptavidin, a derivative thereof, an antigen, or an antibody.

58. A process for detecting a nucleic acid in a sample, wherein the process comprises:
  a) aligning a second nucleic acid on a surface according to claim 1;
  b) contacting the aligned nucleic acid with the nucleic acid in the sample; and
  c) detecting, directly or indirectly, the reaction between the aligned nucleic acid and the sample nucleic acid.

59. A process for detecting a nucleic acid in a sample, wherein the process comprises:
  (a) providing a support having a surface S;
  (b) contacting the surface S with a sample A, the sample A comprising a nucleic acid that binds to a second nucleic acid in a first solvent;
  (c) binding the nucleic acid in the sample to the second nucleic acid;
  (d) anchoring the bound nucleic acids to the surface S;
  (e) contacting the sample A with a medium B to form an A/B interface, wherein said medium B is a gas or a second solvent;
  (f) forming a triple line S/A/B/(meniscus) resulting from the contact between the sample A, the surface S, and the medium B;
  (g) moving the meniscus to align the bound nucleic acids on the surface; and
  (h) detecting, either directly or indirectly, the bound nucleic acids.

60. A process of molecular combing, wherein the process comprises:
  a) providing a surface having one end of a nucleic acid attached thereto;
  b) forming a meniscus between the surface, the nucleic acid, an aqueous solution, and a fluid; and
  c) moving the meniscus relative to the surface to align and anchor the nucleic acid onto the surface;
  wherein the aqueous solution has a pH that results in adsorption to the surface by only said end of the nucleic acid.

61. The process according to claim 60, wherein the fluid is air.

62. The process according to claim 60, wherein the pH favoring adsorption by the end of the nucleic acid is about 5 to about 6.

63. The process according to claim 60, wherein the pH favoring adsorption by the end of the nucleic acid is about 8 to about 10.

64. A product of the process of any one of the claims 60, 61, 62, or 63, wherein the product comprises the surface on which the nucleic acid is aligned.

65. A process for aligning a nucleic acid on a surface, wherein the process comprises:
  (A) providing a surface having attached thereto one end of a nucleic acid;
  (B) contacting the surface with a solvent;
  (C) forming a meniscus resulting from contact between the solvent, the surface, and a gas; and
  (D) moving the meniscus to align the nucleic acid on the surface.

66. A process for adhering a nucleic acid strand to a support, wherein the process comprises:
  (A) contacting a support comprising a surface, which has one end of a nucleic acid strand anchored thereto, with an aqueous solution having a meniscus resulting from contact of the surface, the aqueous solution, and an atmosphere in contact with the aqueous solution, wherein the nucleic acid strand has another end that is movable in said aqueous solution beyond its anchored end; and
  (B) slowly moving the meniscus to cause the nucleic acid strand to adhere to the surface and to become stationary on the surface after passage of the strand through the meniscus.

67. A process for aligning a nucleic acid strand on a support, wherein the process comprises:
  (A) providing a support comprising a surface having one end of a nucleic acid strand anchored to said surface;
  (B) contacting the surface and the anchored nucleic acid strand with an aqueous solution having a meniscus resulting from contact of the surface, the aqueous solution, and an atmosphere in contact with the aqueous solution, wherein the nucleic acid strand has another end that is movable about its anchored end in the aqueous solution; and
  (C) moving the meniscus relative to the nucleic acid strand to cause the strand to enter the atmosphere and to become substantially linear;
  wherein the resulting linear, nucleic acid strand adheres to the surface and is stationary on the surface after passage of the meniscus.

68. A process for adhering a nucleic acid strand to a support, wherein the process comprises:
- (A) contacting a support comprising a surface, which has one end of a nucleic acid strand anchored thereto, with an aqueous solution having a meniscus resulting from contact of the surface, the aqueous solution, and an atmosphere in contact with the aqueous solution, wherein the nucleic acid strand has another end that is movable in the aqueous solution beyond its anchored end; and
- (B) slowly moving the meniscus to cause the nucleic acid strand to stretch and to adhere to the surface;
- wherein the nucleic acid strand remains stretched and is stationary on the support after passage of the strand through the meniscus.

69. A process for aligning a nucleic acid strand on a support, wherein the process comprises:
- (A) providing a support comprising a surface having one end of a nucleic acid strand anchored to the surface;
- (B) contacting the surface and the anchored nucleic acid strand with an aqueous solution having a meniscus resulting from contact of the surface, the aqueous solution, and an atmosphere in contact with the aqueous solution, wherein the nucleic acid strand has another end that is movable in the aqueous solution about its anchored end; and
- (C) moving the meniscus relative to the nucleic acid strand to cause the strand to stretch and to become substantially linear;
- wherein the resulting linear nucleic acid strand is stationary on said support and remains stretched after passage of the meniscus.

70. A process of molecular combing, wherein the process comprises:
- (A) providing a surface having one end of a nucleic acid attached thereto;
- (B) forming a meniscus from contact of the surface, the nucleic acid, an aqueous solution, and air; and
- (C) moving the meniscus relative to the surface to align and anchor the nucleic acid onto the surface.

71. A process of molecular combing comprising:
- (A) providing a surface having attached directly or indirectly thereto only one end of a nucleic acid strand;
- (B) providing a meniscus in contact with the nucleic acid strand, wherein the meniscus comprises the surface, a solution, and an atmosphere; and
- (C) moving the meniscus relative to the nucleic acid strand to cause the nucleic acid strand to become linear and to adhere to the surface after passage of the meniscus.

72. A process according to any one of claims 65 to 71, wherein the meniscus is moved by removing the surface from the solvent or removing the solvent from the surface.

73. A process according to any one of claims 65 to 71, wherein the movement of the meniscus is achieved by evaporation of the solvent.

74. A process according to any one of claims 65 to 71, wherein the meniscus is an air/water meniscus.

75. A process according to any one of claims 65 to 71, wherein the surface is a silicon, an oxide of a semiconductor element, or a combination thereof.

76. Product of the process of claim 65, wherein the product comprises the surface on which the nucleic acid is aligned.

77. Product of the process of claim 66, wherein the product comprises the surface on which the nucleic acid is adhered.

78. Product of the process of claim 67, wherein the product comprises the surface on which the nucleic acid is aligned.

79. Product of the process of claim 68, wherein the product comprises the surface on which the nucleic acid is adhered.

80. Product of the process of claim 69, wherein the product comprises the surface on which the nucleic acid is aligned.

81. Product of the process of claim 70, wherein the product comprises the surface on which the nucleic acid is aligned.

82. Product of the process of claim 71, wherein the product comprises the surface on which the nucleic acid is adhered.

83. A process for detecting a nucleic acid in a sample, wherein the process comprises:
- (A) providing a product as claimed in any one of claims 76 to 82; and
- (B) detecting the nucleic acid strand adhered to the support.

84. A kit comprising:
- (A) the product as claimed in any one of claims 76 to 82; and
- (B) reagents for detection of the nucleic acid strand adhered to the support.

85. A process according to claim 13, wherein the exposed group, after chemical modification, has affinity for the nucleic acid or the molecule with biological activity following the attachment of the attachment group.

* * * * *